United States Patent [19]

Baret et al.

[11] 4,409,247

[45] Oct. 11, 1983

[54] PROCESS FOR HYDROLYZING LACTOSE WITH IMMOBILIZED LACTOSE

[75] Inventors: Jean-Luc A. G. Baret, Moret; Luc A. Dohan, Fontainebleau, both of France

[73] Assignee: Corning Glass Works, Corning, N.Y.

[21] Appl. No.: 269,945

[22] Filed: Jun. 3, 1981

[30] Foreign Application Priority Data

Jun. 6, 1980 [FR] France .............................. 80 12616

[51] Int. Cl.$^3$ ...................... A23C 21/02; C12N 11/14
[52] U.S. Cl. ..................................... 426/41; 435/174; 435/176; 435/177
[58] Field of Search ................. 426/41, 583, 491, 582; 435/174, 176, 177, 180, 206, 207

[56] References Cited

U.S. PATENT DOCUMENTS

| | | | |
|---|---|---|---|
| 2,602,746 | 7/1952 | Meade | 426/583 |
| 3,644,326 | 2/1972 | Pien | 426/582 X |
| 3,666,133 | 11/1962 | Pinckney | 426/491 X |
| 3,852,496 | 12/1974 | Weetall et al. | 435/176 X |
| 4,107,334 | 8/1978 | Tolly | 426/583 X |
| 4,265,924 | 5/1981 | Buhler et al. | 426/582 |

FOREIGN PATENT DOCUMENTS 2110303 2/1972 France .
2242032 9/1974 France .

OTHER PUBLICATIONS

Brodelius, P., Industrial Applications of Immobilized Enzymes, Advances in Biochemical Engineering, vol. 10, 1978 (pp. 94–96).
J. L. Baret, *Industrie Alimentaire et Agricoles*, 95, 957 (1978).
E. K. Okos et al., *J. Food Sci.*, 39, 88 (1974).
L. E. Wierzbicki et al., *J. Food Sci.*, 39, 374 (1974).
L. E. Wierzbicki et al., *J. Dairy Sci.*, 56, 1182 (1973).
R. H. Schmidt et al., *Food Prod. Dev.*, 12, 60 (1978).
R. H. Schmidt, *Cereal Chem.*, 55, 58 (1978) [Chem. Abstr., 88, 188419n].
R. H. Schmidt et al., *J. Food Process. Preserv.*, 1, 263 (1977) [*Chem. Abstr.*, 89, 106134Z (1978)].
R. H. Schmidt et al., *J. Food Sci.*, 43, 613 (1978) [*Chem. Abstr.*, 89, 106170h].
H. H. Weetall et al., *Biotechnol. Bioeng.*, 16, 295, 689 (1974).
L. E. Wierzbicki et al., *Biotechnol. Bioeng.*, 16, 397 (1974).

*Primary Examiner*—David M. Naff
*Attorney, Agent, or Firm*—W. E. Maycock

[57] ABSTRACT

Lactose in whey is hydrolyzed with an immobilized lactase by a process which involves heating the whey to a temperature of from about 45° to about 90° C. for at least about 15 seconds, centrifuging the heated whey while it is still warm, contacting the centrifuged whey with an immobilized lactase, cleaning the immobilized lactase, and disinfecting the immobilized lactase. Preferably, lactase is immobilized on an inorganic support, and cleaning and disinfecting are carried out respectively by contacting the immobilized lactase with a solution of protease and with a solution of substituted diethylenetriamine.

14 Claims, No Drawings

PROCESS FOR HYDROLYZING LACTOSE WITH IMMOBILIZED LACTOSE

BACKGROUND OF THE INVENTION

The present invention relates to a process for hydrolyzing lactose. More particularly, the present invention relates to a process for hydrolyzing lactose, such as that contained in whey, by means of an immobilized lactase.

In 1976, French cheese production reached approximately one million tons, resulting in the production of more than six million tons of whey as a by-product. Such whey contains, per liter, approximately 6 to 9 g. of protein, 45 to 50 g. of lactose, 6 to 8 g. of mineral salts, and 1 to 2 g. of fat. World-wide, the amount of lactose available from whey alone in 1977 totaled almost 3.5 million tons.

In the past, whey was regarded as a waste product and was discharged into sewers or streams and rivers. Because of increasing concerns over environmental pollution, much of the whey is being processed into a variety of animal and human foods. For example, the development of high performance ultrafilters now permits the separation of whey protein from the whey. Such protein is of exceptional value. For example, a 35 percent concentrate of whey protein can replace nonfat dry milk in many food products, such as baked goods, beverages, and frozen desserts. Unfortunately, the separation of proteins from whey results in a liquid fraction, called permeate, which until recently has had little or no value.

With the advent of immobilized enzymes, however, hydrolysis of the lactose in the permeate, either with or without demineralization, has become commercially feasible. Because of the presence of glucose and galactose, hydrolyzed lactose is much sweeter and more soluble than lactose alone. Thus, the hydrolyzed product is a functional sweetener which can be used in the preparation of pastries, milk-based desserts, and frozen confections such as ice cream. Furthermore, the hydrolyzed product is an efficiently fermentable mixture suitable for use as a fermentation substrate in, for example, the brewing and pharmaceutical industries.

Various methods for hydrolyzing lactose are, of course, well known to those having ordinary skill in the art. Enzymatic hydrolysis is especially useful for the production of food-related products and, as already indicated, the use of immobilized enzymes is particularly attractive.

By way of illustration only, H. H. Weetall et al., *Biotechnol. Bioeng.*, 16, 295 (1974), discuss the preparation of immobilized lactase and its use in the enzymatic hydrolysis of acid whey. The enzyme, isolated from both fungi and yeast, was immobilized on airconia-coated porous glass particles. The substrate consisted of either aqueous lactose solution or acid whey permeate.

Additionally, L. E. Wierzbicki et al., *Biotechnol. Bioeng.*, 16, 397 (1974), reported on the hydrolysis of lactose in acid whey using lactase (β-galactosidase) immobilized on porous glass particles with emphasis on the preparation and characterization of a reusable catalyst for the production of low-lactose dairy products. Partially purified lactases from *Aspergillus niger, Lactobacillus helveticus,* and *Saccharomyces lactis* were immobilized on porous glass particles. The substrate consisted of acid whey powder which had been reconstituted in water to the appropriate solids concentration. In some instances, the reconstituted acid whey was deproteinized by heating in a boiling water bath for five minutes.

Finally, H. H. Weetall et al., *Biotechnol. Bioeng.*, 16, 689 (1974), describe the preparation of immobilized lactase as part of continued studies on the enzymatic hydrolysis of lactose. A fungal lactase was employed, immobilized on zirconia-coated controlled-pore glass and porous titania particles. The resulting immobilized enzyme preparations were used for the hydrolysis of lactose in whole sweet whey, whole acid whey, acid whey ultrafiltrate, and pure lactose.

It also is possible to carry out the hydrolysis of the lactose in whey without a prior ultrafiltration step and either with or without demineralization. The product, which still contains proteins, is similar to hydrolyzed permeate and, consequently, it also can be used in the food industry as already described.

Unfortunately, however, the hydrolysis of lactose in whey by means of immobilized enzymes without a prior ultrafiltration step is not without problems, especially on a commercial scale.

Such problems in general are related to the presence in the whey of proteins which tend to deposit on the immobilized enzyme bed, i.e., to coat the immobilized enzyme. The protein coat in turn impedes or even stops the diffusion of lactose to the enzyme and the diffusion of the hydrolysis products, i.e., glucose and galactose, away from the enzyme. Consequently, there is, with the passage of time, an apparent decrease in enzymatic activity. The net effect is to render the use of an immobilized lactase for the hydrolysis of lactose in whole whey impractical on a large-scale, continuous basis. Furthermore, removal of the protein by ultrafiltration prior to hydrolysis tends to remove bacterial contamination, thereby reducing bacterial growth on the immobilized enzyme which contributes to the apparent decrease with time of enzymatic activity and the plugging or clogging of the immobilized enzyme reactor.

It should be apparent, though, that any economical commercial process for the hydrolysis of whole whey must maintain enzymatic activity above some minimum value for an adequate period of time. Consequently, efforts undertaken to find a satisfactory procedure for whey hydrolysis with immobilized enzymes primarily have concentrated on the use of demineralized whey permeate. Although various treatments of the immobilized enzyme bed, such as periodic washing and disinfection (with, for example, acetic acid solutions), have been proposed, there still remains a need for a commercially viable procedure for whole whey hydrolysis, i.e., hydrolysis of whole whey which has not previously been subjected to an ultrafiltration treatment.

SUMMARY OF THE INVENTION

It therefore is an object of the present invention to provide a process for treating whey whereby at least a portion of the lactose contained therein is hydrolyzed into glucose and galactose by means of an immobilized lactase.

It also is an object of the present invention to provide a process for treating whey whereby at least a portion of the lactose contained therein is hydrolyzed into glucose and galactose by means of an immobilized lactase without the need for a prior ultrafiltration treatment.

Another object of the present invention is to provide a process for treating whey whereby at least a portion of the lactose contained therein is hydrolyzed into glucose and galactose by means of an immobilized lactase, which process includes a means of cleaning the immobilized enzyme.

Yet another object of the present invention is to provide a process for treating whey whereby at least a portion of the lactose contained therein is hydrolyzed into glucose and galactose by means of an immobilized lactase, which process includes a means of disinfecting the immobilized enzyme.

Still another object of the present invention is to provide a process for treating whey which, for some applications, eliminates the need for a prior ultrafiltration treatment.

A further object of the present invention is to provide a process for cleaning an immobilized lactase of whey protein deposited thereon.

These and other objects will be apparent to those skilled in the art from a consideration of the specification and claims which follow.

Accordingly, the present invention provides a process for treating whey whereby at least a portion of the lactose contained therein is hydrolyzed into glucose and galactose by means of an immobilized lactase, which process comprises the steps of:

A. heating the whey to a temperature of from about 45° to about 90° C. for at least about 15 seconds;

B. centrifuging the heated whey while it is still warm; and

C. contacting the centrifuged whey with an immobilized lactase under conditions sufficient to hydrolyze at least a portion of the lactose contained therein into glucose and galactose.

The present invention also provides a process for treating acid whey whereby at least a portion of the lactose contained therein is hydrolyzed into glucose and galactose by means of an immobilized lactase, which process comprises the steps of:

A. clarifying the whey;

B. heating the whey to a temperature of from about 45° to about 90° C. for at least about 15 seconds; and C. contacting the heated whey with an immobilized lactase under conditions sufficient to hydrolyze at least a portion of the lactose contained therein into glucose and galactose.

The present invention further provides a process for treating whey in order to remove at least a portion of the protein contained therein, which process comprises the steps of:

A. heating the whey to a temperature of from about 45° to about 90° C. for at least about 15 seconds; and B. centrifuging the heated whey while it is still warm.

The present invention further provides a process for cleaning an immobilized lactase having whey protein deposited thereon, which process comprises contacting the immobilized lactase with a solution of a protease.

DETAILED DESCRIPTION OF THE INVENTION

The method of the present invention is intended for use with a lactase which is bound to a water-insoluble support or carrier. Thus, as is well known in the art, lactase is at least about 80 percent hydrolyzed into glucose and galactose by passing a lactose-containing aqueous solution, e.g., whey and whey permeate, through a column containing an immobilized lactase, typically at a temperature below about 60° C. As already described, the effluent can be partially concentrated to yield a syrup suitable for use as a sweetner in various foods.

Such a procedure can be carried out continuously or as a batch process. A continuous process, of course, is preferred.

The lactase employed in the process of the present invention is produced by a variety of microorganisms, such as fungi, bacteria and yeasts. Fungal lactases perhaps are the most common, e.g., lactases isolated from *Aspergillus niger* and *Aspergillus oryzae*. Techniques for isolating lactases from microorganisms are, of course, well known in the art.

Immobilization of the enzyme on the water-insoluble support or carrier is readily accomplished by various methods which also are known. For a recent review of immobilization techniques, see I. Chibata, Editor, "Immobilized Enzymes", Halsted Press, John Wiley & Sons, Inc., New York, 1978, pp. 1-73. The method of immobilization is not known to be critical. If desired, such supports can be porous, thereby allowing an increased enzyme loading per unit mass of support. In general, enzymes are bound to water-insoluble supports by physical adsorption, ionic binding, covalent binding, or some combination thereof.

The water-insoluble supports generally can be either organic or inorganic. Examples of organic supports include, among others, polyesters, such as poly(ethylene terephthalate); polyamides, such as nylon 6 and nylon 6.6; polyacrylates; polymethacrylates; polyacrylamides; poly(acrylic acid); poly(methacrylic acid); poly(galacturonic acid); poly(aspartic acid); ethylene-maleic anhydride copolymers; polyolefins, such as polyethylene, polypropylene, polybutene, and polybutadiene; polystyrene; poly(aminostyrene); poly(vinyl chloride); poly(vinyl alcohol); poly(vinylidene chloride); cellulose and derivatives thereof; agarose gels; dextran gels and derivatives thereof; polysaccharides; polypeptides; collagen; and the like.

The inorganic supports can be classified as siliceous or nonsiliceous metal oxides. Examples of siliceous supports include, among others, glass, silica, wollastonite, bentonite, cordierite, and the like. Examples of nonsiliceous metal oxides include, among others, alumina, spinel, apatite, nickel oxide, titania, zirconia, and the like.

In general, the water-insoluble support can be in any desired shape or form. The support can be particulate in nature, varying from a finely-divided powder to a coarse granular material, or the support can be a continuous, shaped article such as a flat or curved sheet or pellet, or a three-dimensional article such as a rectangular or cylindrical tube or complex monolith. As a practical matter, however, the support most often will be particulate.

For examples of procedures for immobilizing enzymes on inorganic supports, by way of illustration only, see U.S. Pat. No. 3,519,538 (which corresponds with French Patent No. 2,020,527), U.S. Pat. No. 3,556,945 (which corresponds with French Patent No. 2,001,336), and U.S. Pat. Nos. 3,666,627 and 3,802,997 (which correspond with French Patent No. 2,020,661).

Turning now to the specific process steps which comprise the present invention, in the first step the whey is heated to a temperature of from about 45° to about 90° C. for at least about 15 seconds. Preferably, the time of heating will be in the range of from about 15 minutes to about one hour. Such heating causes a pasteurization of the whey and induces the formation of solid colloidal protein particles in suspension which can be sedimented by centrifugation.

The second step, then, comprises centrifuging the heated whey while it is still warm. The conditions for centrifuging are not critical, provided only that such conditions are sufficient to sediment the solid matter suspended in the heated whey. Such conditions will be readily apparent to one having ordinary skill in the art. By way of illustration only, centrifuge speeds of from about 8,000 to about 12,000 rpm are perhaps typical.

In the third step, the centrifuged whey is contacted with an immobilized lactase under conditions sufficient to hydrolyze at least a portion of the lactose contained therein into glucose and galactose. Such contacting is not critical to the process of the present invention and in general is carried out in accordance with well-known procedures.

Optionally and preferably, the immobilized lactase then is cleaned to remove deposited protein therefrom. Such cleaning can be carried out in accordance with procedures which are well known in the art. More preferably, however, such cleaning is carried out by contacting the immobilized lactase with a solution of a proteolytic enzyme or protease. Most preferably, such solution will have a protease activity of from about 0.1 to about 10 Anson units per liter.

Anson analysis can be used for the determination of the proteolytic activity of most proteases, although the procedure perhaps is best known in Europe. Briefly, denatured hemoglobin is digested under standard conditions. The undigested hemoglobin is precipitated with trichloroacetic acid and the amount of trichloroacetic acid-soluble product is determined spectrophotometrically with phenol reagent which gives a blue color with tyrosine and tryptophan. The color reaction typically is carried out for ten minutes at a pH of 7.5 and a temperature of 25° C. One Anson unit, then, is defined as the amount of enzyme which, under these conditions, digests hemoglobin at an initial rate such that there is liberated per minute an amount of trichloroacetic acid-soluble product which gives the same color with phenol reagent as one milliequivalent of tyrosine.

In general, any protease can be employed which removes the protein coating from the immobilized enzyme without any significant deleterious effect on enzymatic activity. Examples of suitable proteases include, by way of illustration only, neutral proteases from *Bacillus subtilis* and an alkaline protease from *Bacillus licheniformis*.

Such proteases are members of a group of well-known, commercially available enzymes which are widely used in laundry detergent compositions. Examples of commercially available neutral proteases include Protease B 500, which is supplied by Rapidase, the French subsidiary of Gist Brocades, and Neutrase® 0.5 L, supplied by Novo. An example of a commercially available alkaline protease is Alcalase® 0.6 L, also supplied by Novo, and commonly known as subtilisin A.

It is very surprising and unexpected that these proteases, which are very aggressive toward proteinaceous material, clean the immobilized lactase of the protein deposited thereon without attacking the lactase which is itself a proteinaceous substance. This is especially so since such proteases are known to be highly active against the soluble lactase, i.e., lactase which has not been immobilized.

Another optional step, which also is preferred, comprises disinfecting the immobilized lactase. While disinfecting generally can be carried out by any method known to those having ordinary skill in the art, a particularly preferred procedure is that described in U.S. patent application Ser. No. 206,099, filed Nov. 12, 1980, now U.S. Pat. No. 4,393,138, in the name of Jean-Luc Baret, which application is incorporated herein by reference.

As described in said application Ser. No. 206,099, an immobilized enzyme is disinfected by contacting the immobilized enzyme with a dilute aqueous solution of at least one substituted diethylenetriamine at a concentration and for a period of time which is sufficient to kill contaminating microorganisms without significant deleterious effects on the immobilized enzyme.

Such substituted diethylenetriamines are employed in dilute aqueous solutions, typically at a concentration of from about 0.1 to about 0.5 percent by weight, although lower or higher concentrations can be used. In general, the concentration of substituted diethylenetriamine, the total volume of aqueous solution, and the duration of the disinfecting treatment can vary widely, depending, at least in part, on the substituted diethylenetriamine(s) employed, the severity of the microbial contamination, the type(s) of microorganism(s) present, and the amount of immobilized enzyme. Nevertheless, such treatment conditions or parameters are readily determined by those having ordinary skill in the art. Most frequently, however, treatment for about 15-30 minutes with 5 to 10 liters of a 0.1 percent by weight disinfecting solution of, for example, Tego Dioctyl BS, per kilogram of immobilized enzyme has proven satisfactory.

In one embodiment, the immobilized enzyme is simply placed in a bath of disinfecting solution. Optionally, the bath can be shaken, stirred, circulated by a pumping means, or otherwise agitated.

In another embodiment, the disinfecting solution is circulated through the column or reactor containing the immobilized enzyme. Preferably, such circulation of disinfecting solution is carried out in a reverse flow mode, i.e., in the direction opposite to the flow of feed solution through the column or reactor. Where the enzyme has been immobilized on a particulate support and the column or reactor design so allows, the rate of the reverse flow of disinfecting solution desirably is such that the immobilized enzyme particles are fluidized. Such fluidization prevents channeling and ensures complete contact of the immobilized enzyme with disinfecting solution.

The whey which is used in the process of the present invention does not require any pretreatment. Preferably, however, the serum is clarified, e.g., by centrifuging. After clarification, the whey optionally can be demineralized to an extent up to about 90 percent and/or acidified to a pH of from about 3.5 to about 6. Demineralization is carried out by known means, such as by electrodialysis or ion exchange. Acidification also is carried out by known means, with the use of hydrochloric acid being especially suitable. If desired, acidification can be carried out prior to clarification.

Whether or not acidification is carried out depends at least in part on the pH profile of the immobilized lactase and the pH of the whey to be used. For example, acid whey from the production of cottage cheese typically has a pH of from about 4.5 to about 4.7, whereas sweet whey from the production of cheddar cheese has a pH of from about 6 to about 6.6 and, consequently, requires acidification. Demineralization, of course, also can affect the pH of the whey.

While the heat-treatment of the whey generally is followed by centrifugation, under some circumstances such subsequent centrifugation can be omitted. In general, omission of this centrifugation step is possible when (1) the whey has been clarified prior to the heat-treatment step and (2) the whey is an acid whey having a pH at or near the optimum pH for the immobilized lactase, typically a pH of about 4.5, which whey, therefore, needs no acidification prior to hydrolysis of the lactose contained therein.

It should be apparent to one having ordinary skill in the art that the process of the present invention can be either a batch process or a continuous process, with the latter being preferred. In a continuous process, however, cleaning and/or disinfecting, if carried out, are not carried out continuously since doing so would preclude the third step from being carried out at all; rather, these two steps would be carried out periodically, such as daily. In addition, a continuous process does not require that steps A and B also are continuous. If desired, steps A and B can be carried out in a batch-wise fashion.

If desired, two or more immobilized lactase reactors can be mounted in parallel. When it is time for the periodic cleaning and disinfecting of the immobilized lactase in one reactor, the third step can be continued in the second or other reactor to avoid disruption of the process. Other variations, of course, will be readily apparent to those having ordinary skill in the art.

As already suggested, the whey which is treated in accordance with the process of the present invention can be deacidified or neutralized and then concentrated to a syrup by, for example, evaporation. Such syrup, which contains protein, glucose, galactose, and residual unhydrolyzed lactose, has high sweetening power. This sweetening power, combined with the nutritional and functional properties (such as emulsifying, swelling, and combining powers) of the protein, makes the treated whey especially attractive and valuable for use as a food additive.

Furthermore, the process of the present invention is economical since it avoids any use of ultrafiltration and drying operations which are energy intensive.

It should be apparent that the heat-treatment and centrifugation procedures described hereinbefore provide a means for removing from whey at least a portion of the protein contained therein. Thus, such procedures generally will be of value for any application where it is desired to remove at least a portion of the protein present in whey without resorting to ultrafiltration.

The present invention is further illustrated, but not limited, by the examples which follow. Unless otherwise stated, all temperatures are in degrees Celsius and lactase units are International Units.

EXAMPLE 1

Lactase derived from *Aspergillus niger* was immobilized on a particulate silica support by the procedure described in U.S. Pat. No. 3,519,538. Three columns then were charged with approximately equal amounts of the resulting immobilized lactase.

Whole whey was clarified by centrifugation and 50 percent demineralized by electrodialysis. The extent of demineralization was determined by a residual ash measurement and checked by conductance measurements under standard conditions. The resulting demineralized whey was acidified to pH 3.5 with hydrochloric acid. The demineralized whey, initially at a temperature of from 2° to 4°, was heated to 80° with agitation over a period of about one hour. The heated whey was centrifuged while warm at 8000–10,000 rpm, using an Alpha-Laval (LAPX 202) separator with continuous discharge of solids. The supernatent collected was cooled and stored before carrying out the hydrolysis step.

Hydrolysis of the heat-treated whey was carried out at temperatures of 20°, 35°, and 50° (one column per temperature) in order to determine the stability of the immobilized lactase. The heat-treated whey contained 4.53 percent lactose, weight per volume, and had a pH of 3.5. The glucose formed was measured by well-known procedures at the outlet of each column or reactor. Glucose content then was used to calculate the percent conversion of the lactose and the enzymatic activity of the immobilized lactase, again by known means.

The operating conditions and results at each temperature are summarized in Table 1.

TABLE 1

Hydrolysis of Heat-Treated Whey Containing 4.53 Percent Lactose at a pH of 3.5 and at Various Temperatures

|  | Temperature | | |
| --- | --- | --- | --- |
|  | 20° | 35° | 50° |
| Composite (g)[a] | 4.93 | 4.78 | 4.90 |
| A. At the end of 2 hours | | | |
| Flow Rate, (ml/h) | 91 | 107 | 92 |
| % Conversion[b] | 44 | 62 | 80 |
| Eg (u/g) | 79.6 | 210 | 377 |
| B. At the end of 6 hours | | | |
| Flow Rate (ml/h) | 92 | 107 | 93 |
| % Conversion[b] | 44 | 62 | 81 |
| Eg (u/g)[c] | 82 | 214 | 396 |
| C. At the end of 21.5 hours | | | |
| Flow Rate (ml/h) | 82 | 104 | 90 |
| % Conversion[b] | 47 | 62 | 79 |
| Eg (u/g)[c] | 82 | 212 | 355 |

[a]Amount, in grams, of immobilized lactase composite (dry weight).
[b]Percent of lactose converted to glucose.
[c]Specific activity of the immobilized lactase, expressed in units per gram.

Excellent stability of the immobilized lactase was observed at 20° and 35°; after more than 20 hours of continuous operation, no loss was found in comparison with the initial enzymatic activity, based on either percent conversion or specific activity. At 50°, the stability of the immobilized lactase was very good. Although the specific activity decreased about 6 percent from the initial value, the percent conversion data suggest a loss of activity of only 1–2 percent.

Whether or not enzymatic deactivation took place is best seen by comparing the specific activities after two and six hours, respectively. Such comparison is summarized in Table 2.

TABLE 2

Characteristics of Deactivation of Immobilized Lactase During Hydrolysis of Heat-Treated Whey at pH 3.5 and Various Temperatures

|  | Temperature | | |
| --- | --- | --- | --- |
|  | 20° | 35° | 50° |
| Eg2[a] | 79.6 | 210 | 377 |
| Eg6[b] | 82 | 214 | 396 |
| Eg21.5[c] | 82 | 212 | 355 |
| Eg2 − Eg6[d] | 0 | 0 | 0 |
| Deact. Rate[e] | 0 | 0 | 0 |
| Apparent Half-Life[f] | α | α | α |
| Eg2 − Eg21.5[d] | 0 | 0 | 22 |
| Deact. Rate[g] | 0 | 0 | 1.1 |
| Apparent Half-Life[f] | α | α | 171 |
| Eg6 − Eg21.5[d] | 0 | 2 | 41 |
| Deact. Rate[h] | 0 | 0.1 | 2.6 |

TABLE 2-continued

Characteristics of Deactivation of Immobilized Lactase During Hydrolysis of Heat-Treated Whey at pH 3.5 and Various Temperatures

| | Temperature | | |
|---|---|---|---|
| | 20° | 35° | 50° |
| Apparent Half-Life[f] | α | 1980 | 76 |

[a]Specific activity in units per gram at the end of 2 hours
[b]Specific activity in units per gram at the end of 6 hours
[c]Specific activity in units per gram at the end of 21.5 hours
[d]If the algebraic difference is a negative number, the difference is presumed to be zero.
[e](Eg − Eg)/4, expressed as (u/g)/h.
[f]In hours
[g]($Eg^2 - Eg^{21.5}$)/19.5, expressed as (u/g)/h.
[h]($Eg^6 - Eg^{21.5}$)/15.5, expressed as (u/g)/h.

EXAMPLE 2

Comparative Experiments

Five immobilized lactase columns were prepared as described in Example 1 and each was used to hydrolyze whey. The feed for column 1 was whole or crude whey acidified to pH 3.5 with hydrochloric acid. The feed for column 2 was whey which had been clarified by centrifuging and then acidified to pH 3.5 with hydrochloric acid. The feed for columns 3, 4, and 5 was whey which had been clarified by centrifuging, 50 percent demineralized by electrodialysis, and acidified to pH 3.5 with hydrochloric acid. During hydrolysis, glucose measurements were made as in Example 1.

After six hours of continuous operation (Test A), the experiments were stopped and each column was rinsed with water under standard conditions. In each case, the immobilized lactase was cleaned for 20 minutes with 1 percent aqueous acetic acid solution under fluidizing reverse flow conditions. Hydrolysis then was resumed (Test B) under the same conditions as before.

The data obtained are summarized in Tables 3–5, inclusive.

TABLE 3

Hydrolysis of Whole Whey at pH 3.5 and 50°[a]

| | Test A | Test B |
|---|---|---|
| Flow Rate (ml/h) | 102 | 103 |
| Composite (g) | 4.68 | 4.68 |
| Lactose Content, % | 4.26 | 4.26 |
| At the end of 2 hours | | |
| Glucose Content (g/l) | 17 | 16.5 |
| % Conversion | 78 | 76 |
| Eg (u/g) | 402 | 350 |
| At the end of 6 hours | | |
| Glucose Content (g/l) | 11.8 | 11.4 |
| % Conversion | 54 | 53 |
| Eg (u/g) | 142 | 133 |

[a]Data from column 1.

TABLE 4

Hydrolysis of Clarified Whey at pH 3.5 and 50°[a]

| | Test A | Test B |
|---|---|---|
| Flow Rate (ml/h) | 110 | 111 |
| Composite (g) | 4.8 | 4.8 |
| Lactose Content, % | 4.04 | 4.04 |
| At the end of 2 hours | | |
| Glucose Content (g/l) | 17.5 | 17.6 |
| % Conversion | 85 | 85 |
| Eg (u/g) | 520 | 543 |
| At the end of 6 hours | | |
| Glucose Content (g/l) | 14.1 | 14.4 |
| % Conversion | 68 | 70 |

TABLE 4-continued

Hydrolysis of Clarified Whey at pH 3.5 and 50°[a]

| | Test A | Test B |
|---|---|---|
| Eg (u/g) | 251 | 269 |

[a]Data from column 2.

TABLE 5

Hydrolysis of Clarified and Demineralized Whey at pH 3.5 and Various Temperatures

| | 20°[a] | | 35°[b] | | 50°[c] | |
|---|---|---|---|---|---|---|
| | Test A | Test B | Test A | Test B | Test A | Test B |
| Flow Rate (ml/h) | 98 | 91 | 107 | 107 | 92 | 92 |
| Composite (g) | 4.93 | 4.93 | 4.78 | 4.78 | 4.90 | 4.90 |
| Lactose Content, % | 4.04 | 4.04 | 4.04 | 4.04 | 4.04 | 4.04 |
| At the end of 2 hours | | | | | | |
| Glucose Content (g/l) | 9.8 | 10.9 | 14.1 | 14.2 | 16[d] | 15.9 |
| % Conversion | 48 | 53 | 68 | 69 | 78 | 77 |
| Eg (u/g) | 96 | 110 | 247 | 257 | 305 | 295 |
| At the end of 6 hours | | | | | | |
| Glucose Content (g/l) | 10.1 | 10.7 | 12.3 | 12.7 | 12.8 | 12.8 |
| % Conversion | 49 | 52 | 60 | 62 | 62 | 62 |
| Eg (u/g) | 97 | 103 | 175 | 186 | 160 | 160 |

[a]Data from column 3.
[b]Data from column 4.
[c]Data from column 5.
[d]After three hours For convenience, the characteristics of enzymatic deactivation are summarized in Table 6.

TABLE 6

Characteristics of Deactivation of Immobilized Lactase During Hydrolysis of Various Whey Feeds at pH 3.5 and Various Temperatures

| | Temp. | $Eg^{2a}$ | $Eg^{6b}$ | <$Eg^c$ | Deact. Rate[d] | Apparent Half-Life[e] |
|---|---|---|---|---|---|---|
| *Whole Whey* | | | | | | |
| Test A | 50° | 402 | 142 | 260 | 65 | 3.1 |
| Test B | 50° | 350 | 133 | 217 | 54 | 3.2 |
| *Clarified Whey* | | | | | | |
| Test A | 50° | 520 | 251 | 269 | 67 | 3.9 |
| Test B | 50° | 543 | 269 | 274 | 68.5 | 4.0 |
| *Clarified and Demineralized Whey* | | | | | | |
| Test A | 20° | 96 | 97 | 0 | 0 | ∞ |
| Test B | 20° | 110 | 103 | 7 | 1.75 | 31.4 |
| Test A | 35° | 247 | 175 | 72 | 18 | 6.9 |
| Test B | 35° | 257 | 186 | 71 | 17.8 | 7.2 |
| Test A | 50° | 305[f] | 160 | 145 | 48.3[g] | 3.2 |
| Test B | 50° | 295 | 160 | 135 | 33.8 | 4.4 |

[a]Specific activity at the end of 2 hours.
[b]Specific activity at the end of 6 hours.
[c]$Eg^2 - Eg^6$ (If $Eg^6$ is larger than $Eg^2$, the difference is presumed to be zero).
[d]<Eg/4, expressed as (u/g)/h, i.e., the hourly decrease in specific activity which is expressed as units per gram.
[e]In hours.
[f]Based on a glucose measurement taken at the end of 3 hours.
[g]<Eg/3

Based on an examination of the above data, the following conclusions can be drawn:

(1) the decrease in enzymatic activity was rapid, except at 20° (for each test, compare $Eg^6$ with $Eg^2$);

(2) the effect of increasing temperatures was marginal, since percent conversion leveled off while enzymatic activity peaked and then decreased;

(3) the decrease in enzymatic activity was reversible, since cleaning restored the activity to its initial level (compare specific activities for Tests A and B after either two or six hours);

(4) at 35° and 50°, the immobilized enzyme had too short a half-life for commercial applications; and (5) at 20°, the immobilized enzyme half-life appeared to be satisfactory for commercial applications, but the specific activity was too low.

Taken together, Examples 1 and 2 clearly demonstrate the advantage imparted by heat treatment and centrifugation prior to the hydrolysis of whey by an immobilized lactase. Such advantage is more clearly seen in Table 7 which summarizes and compares the data in Tables 2 and 6.

TABLE 7

Comparison of Immobilized Lactase Deactivation During Hydrolysis of Clarified and Demineralized Whey With and Without Heat Treatment

| | Temp. | Deactivation Rate | Apparent Half-Life |
|---|---|---|---|
| Without Heat Treatment | 35° | 17.9[a] | 7[a] |
| With Heat Treatment | 35° | 0.1[b] | 1980[b] |
| Without Heat Treatment | 50° | 41[a] | 3.8[a] |
| With Heat Treatment | 50° | 1.8[c] | 124 |

[a]An average of the values obtained in Tests A and B
[b]Because two of the three calculations resulted in a zero deactivation rate and an infinite half-life, the average values are presumed simply to be lesser than and greater than the single finite values obtained for deactivation rate and half-life, respectively.
[c]Because one of the three calculations resulted in a zero deactivation rate and an infinite half-life, the average values are presumed to be lesser than and greater than the averages of the two finite values obtained for deactivation rates and half-lives, respectively.

As Table 7 clearly shows, the heat treatment and centrifugation of the clarified and demineralized whey prior to hydrolysis improved immobilized enzyme stability, measured in terms of half-life, by a factor of about 30 to about 300, depending upon the temperature. Such an improvement has a considerable impact on the use of an immobilized lactase to hydrolyze whole whey on a commercial scale.

EXAMPLE 3

This example demonstrates the additional advantages which result from the cleaning and disinfecting steps of the process of the present invention.

Each week, approximately 100 l of whole whey was received from a cheese factory. Upon receipt, the whey was clarified by centrifuging in an Alpha-Laval LAPX 202 separator operating at 11,000–12,000 rpm and with a flow rate of 30–35 l/h. The clarified whey was demineralized by approximately 50 percent in a Stackpack electrodialysis module (Ionics). The resulting clarified and demineralized whey was acidified to pH 3.5 by the addition of about 0.7 to 1 g of concentrated hydrochloric acid per liter of whey. The acidified whey then was stored at about 2° to 4°.

Each day, approximately 10 l of acidified whey was removed from storage and heated to 80° over a period of about 45 minutes. The warm whey was centrifuged under the conditions described above for clarifying. The whey then was cooled and stored at about 4°. The whey subsequently was used as the feed for three immobilized lactase whey hydrolysis columns.

Each column was charged with about 4.7 to 5 g. of the immobilized lactase composite described in Example 1. The flow rate used during hydrolysis was from about 100 to about 110 ml/h. The hydrolysis temperature was 35° and hydrolysis was conducted continuously or about 18 hours.

At the end of the hydrolysis phase, each column was rinsed with water for about 45 minutes. Each column then was cleaned and/or disinfected as follows:

Column 1

The column was cleaned by passing through the column a solution of the protease, Alcalase ® 0.6L, having a pH of 7.5 and containing 6 Anson units per liter. Such solution was circulated for 20 minutes in a reverse flow mode under fluidizing conditions.

The column then was disinfected by similarly circulating through the column a 0.1 percent solution of Tego Diocto BS which is a mixture of dioctyldiethylenetriamine and trioctyldiethylenetriame sold commercially by the German firm, Th. Goldschmidt A. G.

Finally, the column was again rinsed with water.

Column 2

The column was cleaned and rinsed as described for column 1, except that the cleaning solution was aqueous acetic acid having a pH of 3.

Column 3

The column was disinfected and rinsed as described for column 1.

The hydrolysis and cleaning and/or disinfecting cycles then were repeated for from 17 to 26 days, depending upon the column. The performances of the columns were measured each day at various times as already described. The results obtained are summarized in Table 8, although only specific activities are reported for simplicity. Table 9 summarizes the stabilities and half-lives calculated from the data obtained.

TABLE 8

Hydrolysis of Heat-Treated Whey at pH 3.5 and 35° in Conjunction with Cleaning and/or Disinfecting Steps

| | Column 1 | | | Column 2[c] | | | Column 3 | | |
|---|---|---|---|---|---|---|---|---|---|
| Day | Eg² | Eg | Eg[17b] | Eg² | Eg[a] | Eg[17b] | Eg² | Eg[a] | Eg[17b] |
| 1 | 234 | 235 | 222 | 273 | 258 | 206 | 193 | 174 | 155 |
| 5 | 238 | 296 | 273 | 231 | 202 | 177 | 139 | 143 | 140 |
| 10 | 210 | 233 | 219 | 182 | 163 | 111 | 123 | 125 | 98 |
| 15 | 222 | 220 | — | 162 | 117 | 91 | 114 | 122 | 96.5 |
| 17 | 204 | 223 | 210 | 81 | 36 | 13 | 112 | 107 | 97 |
| 20 | 223 | 213 | 203 | | | | 117 | 104 | 104 |
| 26 | 198 | 203 | 175 | | | | 103 | 98 | 90 |

[a]Average specific activity in units per gram over 15 hours of continous production.
[b]Specific activity in units per gram at the end of 17 hours.
[c]Hydrolysis terminated on the 17th day.

TABLE 9

Summary of Stabilities and Half-Lives During Hydrolysis of Heat-Treated Whey at pH 3.5 and 35° in Conjunction With Cleaning and/or Disinfecting Steps

| | Acetic Acid Only | Tego Diocto BS Only | Protease, Tego Diocto BS |
|---|---|---|---|
| Half-Life Days | 9 | 35 | 55 |
| Stability, %[a] | 60 | 90 | 95 |

[a]Stability is the average statistical ratio, expressed as percent of the activity at the end of 17 hours of operation to the activity at the end of 2 hours of operation, over all of the days of operation.

From Tables 8 and 9, it is seen that:

(1) the column disinfected with acetic acid showed a rather rapid decrease in performance as measured by the specific activity of the immobilized lactase. The decrease in activity per unit time became significantly greater after the 15th day, which led to the column being shut down at the end of the 17th day;

(2) compared with the column disinfected with acetic acid, the column cleaned with Tego Diocto BS had a much improved stability and half-life. Thus, the control of the microbial contamination with the column permits obtaining an important benefit at the commercial level; and (3) the most interesting results were obtained by combining a cleaning step employing a protease solution and a disinfecting step using a solution of at least one substituted diethylenetriamine, e.g., Tego Diocto BS, with the heat treatment disclosed herein, which combination gave a decisive gain in stability and half-life.

EXAMPLE 4

The purpose of this example is to determine the change in the performance of the immobilized lactase used to hydrolyze whole whey as a function of the number of hydrolysis/cleaning cycles. The immobilized lactase was prepared as described in Example 1. Each hydrolysis phase lasted 18 hours and six cycles were carried out. The conditions for hydrolysis and cleaning were as follows:

Hydrolysis

The feed was whole whey acidified to pH 3.5 with hydrochloric acid. The temperature was 32°, and 4.2 g. (dry weight basis) of immobilized lactase was used.

Cleaning

The column first was rinsed with water for 45 minutes and then was cleaned with acetic acid as described in Example 3. The final water rinse was carried out for 3 minutes.

The results obtained are summarized in Table 10.

TABLE 10

Multiple Hydrolysis/Cleaning Cycles Using Whole Whey at pH 3.5 and 32° and an Acetic Acid Cleaning Solution

| Cycle No. | Average Performance During Hydrolysis[a] | | |
|---|---|---|---|
| | Flow Rate (ml/h) | % Conversion | Eg (u/g) |
| 1 | 114 | 49.3 | 144 |
| 2 | 98 | 56 | 149 |
| 3 | 99 | 46 | 98 |
| 4 | 94 | 40 | 71 |
| 5 | 96 | 42.6 | 83 |
| 6 | 94 | 35 | 55 |

[a]The average was calculated over 15.5 hours of continous hydrolysis (the first 2.5-hour period was excluded).

An examination of the above results shows that:

(1) the half-life of the immobilized lactase is very low (a little less than five days, based on specific activity values);

(2) the acetic acid cleaning does not guarantee an adequate stability of the immobilized lactase during the consecutive hydrolysis/cleaning cycles; and (3) the results obtained do not permit consideration of the hydrolysis/cleaning cycle employed for use on a commercial scale because of the rapid loss of enzymatic activity.

What is claimed is:

1. A process for treating whey whereby at least a portion of the lactose contained therein is hydrolyzed into glucose and galactose by means of an immobilized lactase, which process comprises the steps of:
A. heating the whey to a temperature of from about 45° to about 90° C. for at least about 15 seconds;
B. centrifuging the heated whey while it is still warm;
C. contacting the centrifuged whey with an immobilized lactase under conditions sufficient to hydrolyze at least a portion of the lactose contained therein into glucose and galatose;
D. cleaning the immobilized lactase by contacting the immobilized lactase with a solution of a protease which removes protein coating the immobilized lactase without significant deleterious effects on the enzymatic activity of the immobilized lactase; and
E. disinfecting the immobilized lactase by contacting the immobilized lactase with a disinfecting solution which substantially kills the contaminating microorganisms without significant deleterious effects on the immobilized lactase; wherein the lactase is immobilized on an inorganic support.

2. The process of claim 1 in which the time of heating in step A is from about 15 minutes to about one hour.

3. The process of claim 1 or 2 in which the solution of a protease has an enzymatic activity of from about 0.1 to about 10 Anson units per liter of solution.

4. The process of claim 1 or 2 in which step E is accomplished by contacting the immobilized lactase with a dilute aqueous solution of at least one substituted diethylenetriamine which is selected from the group consisting of dioctyldiethylenetriamine and a mixture of dioctyldiethylenetriamine and trioctyldiethylenetriamine.

5. The process of claims 1 or 2 in which step A is carried out with a whey previously demineralized to an extent of up to about 90 percent.

6. The process of claims 1 or 2 in which prior to step C the whey is acidified to a pH of from about 3.5 to about 6.

7. The process of claims 1 or 2 in which prior to step A the whey is clarified.

8. A process for treating acid whey whereby at least a portion of the lactose contained therein is hydrolyzed into glucose and galactose by means of an immobilized lactase, which process comprises the steps of:
A. clarifying the whey;
B. heating the whey to a temperature of from about 45° to about 90° C. for at least about 15 seconds;
C. contacting the heated whey with an immobilized lactase under conditions sufficient to hydrolyze at least a portion of the lactose contained therein into glucose and galactose;
D. cleaning the immobilized lactase by contacting the immobilized lactase with a solution of a protease which removes protein coating the immobilized lactase without significant deleterious effects on the enzymatic activity of the immobilized lactase; and
E. disinfecting the immobilized lactase by contacting the immobilized lactase with a disinfecting solution which substantially kills the contaminating microorganisms without significant deleterious effects on the immobilized lactase;
wherein the lactase is immobilized on an inorganic support.

9. The process of claim 8 in which the time of heating in step B is from about 15 minutes to about one hour.

10. The process of claim 8 or 9 in which the solution of a protease has an enzymatic activity of from about 0.1 to about 10 Anson units per liter of solution.

11. The process of claim 8 or 9 in which step E is accomplished by contacting the immobilized lactase with a dilute aqueous solution of at least one substituted diethylenetriamine which is selected from the group consisting of dioctyldiethylenetriamine and a mixture of dioctyldiethylenetriamine and trioctyldiethylenetriamine.

12. The process of claims 8 or 9 in which step B is carried out with a whey previously demineralized to an extent of up to about 90 percent.

13. A process for cleaning an immobilized lactase having whey protein deposited thereon, which process comprises contacting the immobilized lactase with a solution of a protease which removes the whey protein coating the immobilized lactase without significant deleterious effects on the enzymatic activity of the immobilized lactase, wherein the lactase is immobilized on an inorganic support.

14. The method of claim 13 in which the solution of a protease has an enzymatic activity of from about 0.1 to about 10 Anson units per liter of solution.

* * * * *